United States Patent [19]
Fröstl et al.

[11] Patent Number: 5,135,930
[45] Date of Patent: Aug. 4, 1992

[54] HYDROGENATED NITROGEN CONTAINING TETRACYCLES HAVING TWO NONADJACENT LACTAM RINGS

[75] Inventors: Wolfgang Fröstl, Basel; Cesare Mondadori, Aesch; Dietrich Strub, Birsfelden; Armin Züst, Basel, all of Switzerland

[73] Assignee: Ciba-Geigy Corporation, Ardsley, N.Y.

[21] Appl. No.: 621,484

[22] Filed: Dec. 3, 1990

[30] Foreign Application Priority Data

Dec. 8, 1989 [CH] Switzerland .................. 4412/89

[51] Int. Cl.$^5$ .................. C07D 471/16; C07D 487/16; A61K 31/55; A61K 31/495
[52] U.S. Cl. .................. 514/250; 540/556; 544/343
[58] Field of Search .................. 514/250; 544/343

[56] References Cited

U.S. PATENT DOCUMENTS

| | | | |
|---|---|---|---|
| 4,897,399 | 1/1990 | Wasley | 546/66 |
| 4,997,832 | 3/1991 | Wasley | 514/215 |
| 5,015,645 | 5/1991 | Wasley | 514/250 |

FOREIGN PATENT DOCUMENTS 0338989 10/1989 European Pat. Off. .

*Primary Examiner*—Mark L. Berch
*Attorney, Agent, or Firm*—Irving M. Fishman; Karen G. Kaiser

[57] ABSTRACT

Novel hydrogenated heterocyclic compounds, containing two nitrogen atoms, of the formula

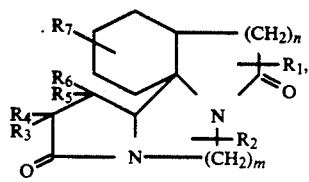

(I)

in which $R_1$, $R_2$, $R_3$, $R_5$ and $R_7$ are each, independently of the others, hydrogen or lower alkyl, m is 2 or 3, n is 1 or 2, and either $R_4$ and $R_6$ are each hydrogen or $R_4$ and $R_6$ together form an additional bond, in free form or in form of a salt, can be used as pharmaceutical active ingredients for memory improvement and can be manufactured in a manner known per se.

11 Claims, No Drawings

HYDROGENATED NITROGEN CONTAINING TETRACYCLES HAVING TWO NONADJACENT LACTAM RINGS

The invention relates to hydrogenated heterocyclic compounds, containing two nitrogen atoms, of the formula

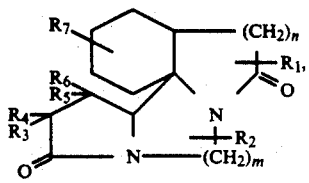

in which $R_1$, $R_2$, $R_3$, $R_5$ and $R_7$ are each, independently of the others, hydrogen or lower alkyl, m is 2 or 3, n is 1 or 2, and either $R_4$ and $R_6$ are each hydrogen or $R_4$ and $R_6$ together form an additional bond, in free form or in form of a salt, to the use of these compounds, to a process for the manufacture of these compounds and to pharmaceutical compositions containing such a compound I in free form or in the form of a pharmaceutically acceptable salt.

Within the scope of the invention, the compounds I may be in the form of stereoisomers. Since the compounds I contain at least three chiral carbon atoms (C-atoms) (that is the C-atoms that are involved in linking the four (theoretical) isolated basic ring structures to the tetracyclic structure shown in formula I), they may be, for example, in the form of pure enantiomers, mixtures of enantiomers, such as racemates, pure diastereoisomers, mixtures of diastereoisomers or mixtures of racemates. Within the scope of the invention preferred compounds I are those having, at the three above-mentioned chiral C-atoms, the sterochemistry disclosed by way of example.

Compounds I in salt form are especially corresponding acid addition salts, preferably pharmaceutically acceptable acid addition salts. These are formed, for example, with strong inorganic acids, such as mineral acids, for example sulfuric acid, a phosphoricacid or a hydrohalic acid, with strong organic carboxylic acids, such as lower alkanecarboxylic acids, for example acetic acid, saturated or unsaturated dicarboxylic acids, for example malonic, maleic or fumaric acid, or hydroxycarboxylic acids, for example tartaric or citric acid, or with sulfonic acids, such as lower alkanesulfonic acids or unsubstituted or substituted benzenesulfonic acids, for example methane- or p-toluene-sulfonic acid. Also includes are salts that are suitable for pharmaceutical uses, since these can be used, for example, for the isolation or purification of free compounds I and their pharmaceutically acceptable salts.

Throughout this specification, radicals or compounds designated "lower" are to be understood as those having up to and including 7, especially up to and including 4, carbon atoms, unless otherwise specified.

Lower alkyl is $C_1$-$C_4$alkyl, i.e., methyl, ethyl, n-propyl, isopropyl, n-butyl, isobutyl, sec.-butyl or tert.-butyl and also includes $C_5$-$C_7$alkyl radicals, i.e. corresponding pentyl, hexyl or heptyl radicals.

Halogen is halogen having an atomic number of up to and including 53, i.e. chlorine or bromine, or also fluorine or iodine.

The compounds I possess, for example, valuable pharmacological, especially nootropic, properties.

In, for example, the Two-Compartment Passive Avoidance test model [according to Mondadori and Classen, Acta Neurol. Scand. 69, Suppl. 99, 125 (1984)], they cause a distinct reduction in the amnesic effect of a cerebral electric shock in mice at dosages of approximately 0.3 mg/kg and above i.p. and p.o.

The compounds I also have a considerable memory-improving action, which can be observed in the Stepdown Passive Avoidance Test [according to Mondadori and Waser, Psychopharmacol. 63, 297 (1979)] in mice at a dosage of approximately 0.3 mg/kg and above p.o.

Furthermore, the compounds I have a significant memory-refreshing activity, which can be demonstrated by way of the Step-through Dark Avoidance Test model in mice at a dosage of approximately 0.3 mg/kg and above p.o.

Accordingly, the compounds I, in free form or in form of a pharmaceutically acceptable salt, can be used, for example, as active ingredients in nootropics that are used, for example, for the treatment of cerebral deficiency phenomena, especially memory disorders. The invention thus relates to the use of compounds I, in free form or in form of a pharmaceutically acceptable salt, for the manufacture of corresponding medicaments. The commercial preparation of the active ingredients is also included.

Preferred within the scope of the invention are compounds of the formula I, in which $R_1$, $R_2$, $R_3$, $R_5$ and $R_7$ are each, independently of the others, hydrogen or lower alkyl, m is 2 or 3, n is 1 or 2, and $R_4$ and $R_6$ are each hydrogen, in free form or in form of a salt.

Especially preferred within the scope of the invention are compounds of the formula I, in which $R_1$, $R_2$, $R_3$, $R_5$ and $R_7$ are each, independently of the others, hydrogen or lower alkyl, m is 2, n is 1, and either $R_4$ and $R_6$ are each hydrogen or $R_4$ and $R_6$ together form an additional bond, in free form or in form of a salt.

Especially preferred within the scope of the invention are compounds of the formula I, in which $R_1$, $R_2$, $R_3$, $R_5$ and $R_7$ are each, independently of the others, hydrogen or lower alkyl, m is 2, n is 1, and $R_4$ and $R_6$ are each hydrogen, in free from or in form of a salt.

Especially preferred within the scope of the invention are compounds of the formula I, in which $R_1$, $R_2$, $R_3$, $R_5$ and $R_7$ are each hydrogen, m is 2, n is 1, and either $R_4$ and $R_6$ are each hydrogen or $R_4$ and $R_6$ together form an additional bond, in free form or in form of a salt.

Most preferred within the scope of the invention are compounds of the formula I, in which $R_1$, $R_2$, $R_3$, $R_5$ and $R_7$ are each hydrogen, m is 2, n is 1, and $R_4$ and $R_6$ are each hydrogen, in free form or in form of a salt.

Specifically preferred within the scope of the invention are the compounds of the formula I mentioned in the Examples, in free form or in the form of a salt.

The present invention also relates to a process for the manufacture of compounds of the formula I, which process comprises, for example, a) for the manufacture of compounds I, in which $R_4$ and $R_6$ together form an additional bond, oxidising a compound of the formula

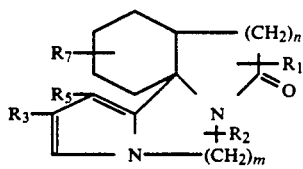

or a salt thereof or b) for the manufacture of compounds I, in which $R_4$ and $R_6$ are each hydrogen, in a compound of the formula

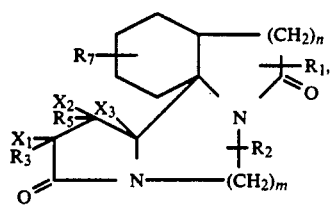

in which either $X_1$ and $X_2$ together are an additional bond and $X_3$ is hydrogen, or $X_1$ is hydrogen and $X_2$ and $X_3$ together are an additional bond, or in a salt thereof, reducing to a single bond the double bond between the carbon atoms carrying the radicals $X_1$ and $X_2$ or between the carbon atoms carrying the radicals $X_2$ and $X_3$ and, if desired, in each case separating a mixture of isomers obtainable in accordance with the process into its components and/or converting a free compound I obtainable in accordance with the process into a salt or conveying a salt obtainable in accordance with the process into the free compound I or into a different salt.

The reactions described hereinbefore and hereinafter are carried out in a manner known pre se, for example in the absence or usually in the presence of a suitable solvent or diluent or a mixture thereof, the reactions being carried out, as required, with cooling, at room temperature or with heating, for example in a temperature range of approximately from $-80°$ C. to the boiling temperature of the reaction medium, preferably from approximately $-20°$ C. to approximately $150°$ C. and, if necessary, in a closed vessel, under pressure, in an inert gas atmosphere and/or under anhydrous conditions.

The starting material mentioned hereinbefore and hereinafter are used for the manufacture of compounds I are known or can be manufactured according to methods known per se, for example in accordance with the procedures described hereinafter.

The information given hereinbefore regarding the salts of compounds I applies in an analogous manner also to the salts of the starting materials.

The oxidation according to process variant a) can be carried out by various methods.

For example, compounds II or salts thereof can be oxidised by reaction with a peroxo compound, for example with hydrogen peroxide or a salt thereof, such as sodium peroxide, peroxodisulfuric acid or a salt thereof, such sodium peroxodisulfate, or an organic peracid, such as performic acid, peracetic acid or an unsubstituted or substituted, for example halogenated, perbenzoic acid, such as perbenzoic acid or m-chloroperbenzoic acid, in the presence of a solvolysis agent, for example water, an alcohol, for example a lower alkanol, such as ethanol, or an acid, for example an organic carboxylic acid, such as an unsubstituted or halogenated lower alkanecarboxylic acid, such as formic acid, acetic acid or trifluoroacetic acid. Depending on the oxidation conditions, $\alpha,\beta$-unsaturated lactams, $\beta,\gamma$-unsaturated lactams or mixtures of the two types of lactam (which can generally be separated into the components in customary manner, for example by chromatography) can be obtained in this oxidation process. Suitable oxidation conditions for the formation of the desired $\alpha,\beta$-unsaturated lactams are the conditions customarily applied for such oxidations and are advantageously those specified in the Examples, the desired $\alpha,\beta$-unsaturated lactam being isolated from the mixture of the two mentioned types of lactam in the case that such a mixture is obtained.

It is, however, also possible for compounds II or salts thereof first of all to be converted with a suitable halogenating agent, such as an N-halosuccinimide, for example N-bromosuccinimide or N-chlorosuccinimide, into the halogenated compounds of formula

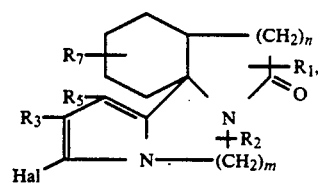

in which Hal is halogen, preferably chlorine or especially bromine, or salts thereof, and for these then to be solvolysed in a second step to compounds I, in which $R_4$ and $R_6$ together form and additional bond, for example by means of one of the afore-mentioned solvolysis agents, if appropriate in the presence of suitable catalysts, such as heavy metal catalysts, for example platinum catalysts, such as tetrakis(triphenylphosphane)palladium(O). Suitable halogenation and solvolysis conditions are the conditions customarily applied for such reactions and are advantageously those specified in the Examples.

Compounds of formula II and salts thereof are known or can be manufactured analogously to known materials.

Depending on the position of the double bond to be reduced, the starting materials III for the process variant b) can be used either in the form of $\alpha,\beta$-unsaturated lactams ($X_1+X_2$=bond; $X_3$=hydrogen) or in the form of $\beta,\gamma$-unsaturated lactams ($X_1$=hydrogen; $X_2+X_3$=bond) or in the form of mixtures of $\alpha,\beta$-unsaturated and $\beta,\gamma$-unsaturated lactams. The $\alpha,\beta$-unsaturated lactams are identical with the compounds I obtainable according to process variant a), in which $R_4$ and $R_6$ together form an additional bond.

The reduction of the carbon-carbon double bond to a single bond in the unsaturated lactams III is carried out in customary manner by treatment with a suitable reducing agent, for example by hydrogenation in the presence of a hydrogenation catalyst, by reduction with a hydride-transferring reagent or by reduction with a metal reduction system comprising a metal and a proton-removing agent.

Suitable hydrogenation catalysts are, for example, elements of sub-group VIII of the Periodic Table of Elements or derivatives thereof, such as palladium, platinum, platinum oxide, ruthenium, rhodium, tris(triphenylphosphane)rhodium(I)halide, for example tris(- triphenylphosphane)rhodium(I) chloride, or Raney nickel, which are optionally applied to a carrier, such as activated carbon, an alkali metal carbonate or sulfate or a silica gel. There come into consideration as hydride-transferring reagents, for example, suitable light metal hydrides, especially alkali metal aluminum hydrides and borohydrides, such as lithium aluminium hydride, lithium triethylborohydride, sodium borohydride, sodium cyanoborohydride or tin hydrides, such as triethyltin or tributyltin hydride, or diborane. The metal component of a metal reduction system is, for example, a base metal, such as an alkali metal or alkaline earth metal, for example lithium, sodium, potassium, magnesium or calcium, or a transition metal, for example zinc, tin, iron or titanium, and there come into consideration as proton-removing agents, for example, protonic acids of the kind mentioned hereinbefore in the definition of acid addition salts, such as hydrochloric or acetic acid, lower alkanols, such as ethanol, and/or amines or ammonia. Examples of such systems are sodium/ammonia, zinc/hydrochloric or acetic acid, or zinc/ethanol.

The reduction of compounds III and salts thereof is carried out, for example, in the presence of a suitable inert solvent or diluent, such as an unsubstituted or halogenated hydrocarbon, for example hexane, cyclohexane, benzene, toluene, dichloromethane or chlorobenzene, an ether, for example diethyl ether, dioxan or tetrahydrofuran, or a ketone, for example acetone or 2-butanone, and at room temperature or with gentle heating, for example in a temperature range of from approximately 20° to approximately 100° C.

Especially preferred forms of the reduction process are illustrated in the Examples.

The manufacture of the starting materials III and their salts is carried out in customary manner, for example by oxidation of compounds II or salts thereof, the oxidation being carried out in a manner analogous to that described under process variant a) and the oxidation conditions in each case being selected in such a way that the desired type(s) of the possible types of lactam is(are) obtained. Suitable oxidation conditions are the conditions customarily applied for such oxidations and are advantageously those specified in the Examples.

Salts of compounds I can be produced in a manner known per se. For example acid addition salts of compounds I are obtained by treatment with a suitable acid or a suitable ion exchange reagent. Salts of compounds I can be converted in customary manner into free compounds I; acid addition salts can be converted, for example, by treatment with a suitable basic agent or a suitable ion exchange reagent.

Salts of compounds I can be converted into different salts of compounds I in a manner known per se. Acid addition salts, for example, can be converted into different acid addition salts, for example by treating a salt of an inorganic acid, such as a hydrochloride, with a suitable metal salt, such as a sodium, barium or silver salt, of an acid, for example with silver acetate, in a suitable solvent in which the inorganic salt that is forming, for example silver chloride, is insoluble and thus separates out of the reaction mixture.

Depending on the procedure and on the reaction conditions compounds I having salt-forming properties are obtained in free form or in the form of salts.

Owing to the close relationship between the compound I in free form and in the form of its salts, throughout this specification references to the free compound I or its salts shall, where appropriate, also include the corresponding salts or the free compound I, respectively.

Compounds I, including their salts of salt-forming compounds, can also be obtained in the form of their hydrates and/or may contain other solvents that have been used, for example, for the crystallisation of compounds that exist in solid form.

The compounds I and their salts may be in the form of one of the possible isomers or in the form of a mixture, depending on the starting materials and procedures chosen. Depending on the symmetry of the molecule, for example depending on the number and the absolute and relative configuration of the centres of chirality, such as asymmetric C-atoms, there are obtainable as pure isomers, for example, pure enantiomers and/or pure diastereoisomers, such as pure cis/trans-isomers or meso compounds. Similarly, mixtures of isomers may be, for example, mixtures of enantiomers, such as racemates, mixtures of diastereoisomers or mixtures of racemates. Mixtures of isomers of compounds I in free form or in salt form that are obtainable in accordance with the process or by some other method can be separated into the components in customary manner.

Resulting mixtures of diastereoisomers and mixtures of racemates can be separated into the pure diastereoisomers or racemates in known manner on the basis of the physical-chemical differences between the constituents, for example by fractional crystallisation, distillation and/or chromatography.

Resulting mixtures of enantiomers, such as racemates, can be separated into the enantiomers according to known methods, for example by recrystallisation from an optically active solvent, chromatography on chiral adsorbents, with the aid of suitable microorganisms, by cleaving with specific immobilised enzymes, by the formation of inclusion compounds, for example using chiral crown ethers, in which only one enantiomer is complexed, or by conversion into diastereoisomeric salts, for example by reaction of a basic end product racemate with an optically active acid, such as carboxylic acid, for example tartaric or malic acid, or a sulfonic acid, for example camphorsulfonic acid, and separation of the mixtures of diastereoisomers obtained in this manner, for example on the basis of their different solubilities, into the diastereoisomers from which the desired enantiomer can be freed by the action of suitable agents. Advantageously the more active enantiomer is isolated.

The invention relates also to those forms of the process according to which a compound obtainable as intermediate at any stage of the process is used as starting material and the remaining steps are carried out, or a starting material is used in the form of a derivative or salt and/or its racemates or enantiomers or, especially, is formed under the reaction conditions.

The starting materials and intermediates used in the process according to the present invention, each in free form or salt form, are preferably those that result in the compounds I described at the beginning as being especially valuable.

The invention also relates to novel materials and intermediates, in each case in free form or in salt form, for the manufacture of the compounds I, to the use thereof and to processes for their manufacture, the variables $R_1$, $R_2$, $R_3$, $R_4$, $R_5$, $R_6$, $R_7$, m and n having the meanings given for compounds I.

The invention relates also to the use of compounds I and their pharmaceutically acceptable salts for the treatment of cerebral deficiency phenomena, especially memory disorders, preferably in the form of pharmaceutically acceptable preparations, especially in a method for the therapeutic treatment of the animal or human body, and to such a method of treatment.

The invention relates equally to pharmaceutical preparations hat contain a compound I or a pharmaceutically acceptable salt thereof as active ingredient, and to processes for the manufacture thereof. These pharmaceutical preparations are for enteral, such as oral, and also rectal or parenteral administration to warm-blooded animals, and contain the pharmacologically active ingredient on its own or together with conventional pharmaceutical adjuncts. The pharmaceutical preparations contain, for example, approximately from 0.1% to 100%, preferably from approximately 1% to approximately 50%, active ingredient. Pharmaceutical preparations for enteral and parenteral administration are, for example, those in dosage unit forms, such as drages, tablets, capsules or suppositories and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or drage cores.

Suitable carriers are especially fillers, such as sugers, for example lactose, saccharose, mannitol or sorbitol, cellulose preparations and/or calcium phosphates, for example tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, cross-linked polyvinylpyrrolidone, agar or alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol. Drage cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or drage coatings, for example for the purpose of identification or to indicate different doses of active ingredient.

Other orally administrable pharmaceutical preparations are dry-filled capsules made of gelatin, and also soft, sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules that contain a combination of the active ingredient with a base material. Suitable base materials are, for example, liquid triglycerides, polyethylene glycols or paraffin hydrocarbons.

There are suitable for parenteral administration especially aqueous solutions of an active ingredient in water-soluble form, for example in the form of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran, and, where appropriate, also stabilisers.

The dosage of the active ingredient may depend on various factors, such as mode of administration, warm-blooded species, age and/or individual condition. For oral administration, the approximate daily dosage normally to be recommended for a warm-blooded animal weighing approximately 75 kg is from approximately 20 mg to approximately 1500 mg, especially from approximately 50 to approximately 250 mg, which is advantageously taken in several equal partial doses.

The following Examples illustrate the above-described invention but are not intended to limit the scope thereof in any way. Temperatures are given in degrees Celsius.

EXAMPLE 1 a) 700 mg (2.8 mmol) of (9aR*,9bR*,13aR*)-2,7-dioxo-1,4,5,7,9a,10,11,12,13,13a-decahydro-2H-pyrrolo[2',1':3,4]pyrazino[2,1-i]indole, dissolved in 30 ml of tetrahydr are hydrogenated with hydrogen in the presence of 70 mg of $PtO_2$ at room temperature under normal pressure until the absorption of hydrogen ceases. The catalyst is filtered off and the filtrate is concentrated by evaporation in vacuo. The resulting oil is crystallised from ethyl acetate. In this manner (9aR*,9bR*,13aR*)-2,7-dioxo-1,4,5,7,8,9,9a,10,11,12,13,13a-dodecahydro-2H-pyrrolo[2',1':3,4]pyrazino2,1-i]indole of formula

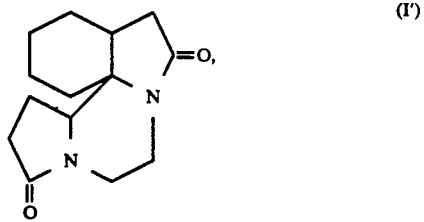

(I')

is obtained, that is to say the compound of formula I in which $R_1$, $R_2$, $R_3$, $R_4$, $R_5$, $R_6$ and $R_7$ are each a hydrogen atom, m is 2, n is 1 and the chiral C-atoms 9a, 9b and 13a have the above relative configuration (each R*) (melting range: 135° to 136°). The mother liquor is concentrated by evaporation in vacuo and chromatographed on silica gel (0.040–0.063 mm) with trichloromethane and trichloromethane/methanol (99:1) as eluants. There is thus obtained (9aR*,9bS*,13aS*)-2,7-dioxo-1,4,5,7,8,9,9a,10,11,12,13,13a-dodecahydro-2H-pyrrolo[2',1':3,4]pyrazino[2,1-i]indole, which is stereoisomeric as regards the relative configuration of the 9a C-atom, in the form of an oil which is crystallised from ethyl acetate and then melts at 177°-179°.

b) The α,β-unsaturated lactam used as starting material can be manufactured, for example, as follows:

4.05 g (20 mmol) of m-chloroperbenzoic acid are added in portions at room temperature, with stirring, to a solution of 2.3 g (10 mmol) of (9bR*,13aR*)-2-oxo-1,4,5,10,11,12,13,13a-octahydro-2H-pyrrolo[2',1':3,4-]pyrazino[2,1-i]indole in 50 ml of dichloromethane (the exothermic reaction is maintained at room temperature using an ice-bath). 2.28 g (20 mmol) of trifluoroacetic acid are then added dropwise to the reaction mixture which is then stirred for 16 hours at room temperature. The reaction mixture is diluted with 100 ml of dichloromethane and then washed in succession with sodium hydrogen sulfite solution (5%) and sodium hydrogen carbonate solution (5%). The organic phase is separated off, dried over sodium sulfate and concentrated by evaporation in vacuo. The crude product obtainable in that manner is chromatographed on 210 g of silica gel (0.040–0.063 mm) using trichloromethane as eluant. In this manner (9aR*,9bR*,13aR*)-2,7-dioxo-1,4,5,7,9a,10,11,12,13,13a-decahydro-2H-pyrrolo[2',1':3,4]pyrazino[2,1-i]indole is obtained in the form of an oil, which is crystallised from dichloromethane/diethyl ether and melts at 159°-162°.

c) The α,β-unsaturated lactam used as starting material can also be manufactured, for example, as follows:

2.3 g (10 mmol) of (9bR*,13aR*)-2-oxo-1,4,5,10,11,12,13,13a-octahydro-2H-pyrrolo[2',1':3,4-]pyrazino[2,1-i]indole are dissolved in 60 ml of absolute tetrahydrofuran. 1.78 g (10 mmol) of N-bromosuccinimide are added in portions, at 0°, to the solution. The reaction mixture is then stirred for 30 minutes at 0° and subsequently left to stand at room temperature for 12 hours. The reddish mixture is substantially concentrated in vacuo, 100 ml of diethyl ether and 100 ml of water are added to the residue, the mixture is extracted by shaking and the organic phase is separated off, washed in succession with 30 ml of 0.5M sodium hydrogen sulfite solution and 1N sodium hydrogen carbonate solution, dried over magnesium sulfate and freed of solvent. The residue is crystallised twice from diethyl ether/pentane. In this manner a mixture consisting of 87% (9bR*,13bR*)7-bromo-2-oxo-1,4,5,10,11,12,13,13a-octahydro-2H-pyrrolo[2',1':3,4]pyrazino[2,1-i]indole and 13% (9bR*,13aR*)-7,8-dibromo-2-oxo-1,4,5,10,11,12,13,13a-octahydro-2H-pyrrolo[2',1':3,4-]pyrazino[2,1-i]indole (melting range of the mixture: 118°-120°) is obtained, which is further used without additional purification.

0.618 g (2 mmol) of this bromide mixture and 0.820 g (10 mmol) of anhydrous sodium acetate are dissolved at room temperature in 40 ml of glacial acetic acid. 0.28 g (0.24 mmol) of tetrakis(triphenylphosphane)palladium(O) is added to the solution under argon. The reaction mixture is stirred for 6 hours at 100°, then cooled and freed of solvent in vacuo. The residue is taken up in dichloromethane and the undissolved portions are filtered off over celite. The filtrate is washed with 1N sodium hydrogen carbonate solution and dried over magnesium sulfate. After removal of the solvent, a viscous red oil remains from which the pure (9aR*,9bR*,13aR*)-2,7-dioxo-1,4,5,7,9a,10,11,12,13,13a-decahydro-2H-pyrrolo[2',1':3,4]pyrazino[2,1-i]indole can be separated by preparative thin layer chromatography [silica gel; eluant: toluene/ethanol/concentrated ammonia (90:20:1)] which, after recrystallisation from ethyl acetate/diethyl ether/pentane, melts at 160°-162°.

EXAMPLE 2

985 mg (4 mmol) of (9bR*,13aR*)-2,7-dioxo-1,4,5,7,8,10,11,12,13,13a-decahydro-2H-pyrrolo[2',1':3,4]pyrazino[2,1-i]indole, dissolved in 40 ml of tetrahydrofuran, are hydrogenated with hydrogen in the presence of 98 mg of PtO$_2$ at room temperature under normal pressure until the absorption of hydrogen ceases. The catalyst is filtered off and the filtrated is concentrated by evaporation in vacuo. The resulting oily crude product is crystallised from ethyl acetate. In this manner (9aR*,9bR*,13aR*)-2,7-dioxo-1,4,5,7,8,9,9a,10,11,12,13,13a-dodecahydro-2H-pyrrolo[2',1':3,4]pyrazino[2,1-i]indole is obtained which melts at 135° to 136°. The mother liquor is concentrated by evaporation in vacuo and chromatographed on silica gel (0.040–0.063 mm) with trichloromethane and trichloromethane/methanol (99:1) as eluants. There is thus obtained (9aR*,9bS*,13aS*)-2,7-dioxo-1,4,5,7,8,9,9a,10,11,12,13,13a-dodecahydro-2H-pryrrolo[2',1':3,4]pyrazino[2,1-i]indole, which is stereoisomeric as regards the relative configuration of the 9a C-atom, in the form of an oil which is crystallised from ethyl acetate and then melts at 177°-179°.

The β,γ-unsaturated lactam used as starting material can be manufactured, for example, as follows:

A solution of 3.04 g (15 mmol) of m-chloroperbenzoic acid in 30 ml of dichloromethane is added dropwise over a period of 45 minutes, at −15° with stirring, to a solution of 2.3 g (10 mmol) of (9bR*,13aR*)-2-oxo-1,4,5,10,11,12,13,13a-octahydro-2H-pyrrolo[2',1':3,4-]pyrazino[2,1-i]indole in 30 ml of dichloromethane. The reaction mixture is then stirred for 4 hours at −15°, then diluted with 100 ml of dichloromethane and washed in succession, ice-cold, with sodium hydrogen sulfite solution (5%) and sodium hydrogen carbonate solution (5%). The organic phase is separated off, dried over sodium sulfate and concentrated by evaporation in vacuo. In this manner a crude product is obtained, which is chromatographed on 120 g of silica gel (0.040–0.063 mm) using trichloromethane as eluant. The desired (9bR*,13aR*)-2,7-dioxo-1,4,5,7,8,10,11,12,13,13a-decahydro-2H-pyrrolo[2',1':3,4]pyrazino[2,1-i]indole is obtained from the appropriate fractions in the form of a foam, which is crystallised from dichloromethane/diethyl ether and then melts at 105° to 125°. Also obtained is the (9aR*,9bR*,13aR*) isomer of 2,7-dioxo-1,4,5,7,9a,10,11,12,13,13a-decahydro-2H-pryrrolo[2',1':3,4]pyrazino[2,1-i]indole in the form of an oil, which is crystallised from dichloromethane/diethyl ether and then melts at 159° to 162°.

EXAMPLE 3

A solution of 3.04 g (15 mmol) of m-chloroperbenzoic acid in 30 ml of dichloromethane is added dropwise over a period of 45 minutes at −15°, with stirring, to a solution of 2.3 g (10 mmol) of (+)-(9bR*,13aR*)-2oxo-1,4,5,10,11,12,13,13a-octahydro-2H-pyrrolo[2',1':3,4-]pyrazino[2,1-i]indole in 30 ml of dichloromethane. The reaction mixture is then stirred for 4 hours at −15°, then diluted with 100 ml of dichloromethane and washed in succession, while ice-cold, with sodium hydrogen sulfite solution (5%) and sodium hydrogen carbonate solution (5%). The organic phase is separated off, dried over sodium sulfate and concentrated by evaporation in vacuo. The (+)-(9bR*,13aR*)-2,7-dioxo-1,4,5,7,8,10,11,12,13,13a-decahydro-2H-pyrrolo[2',1':3,4]pyrazino[2,1-i]indole is obtained in the form of a foam, which can be further reacted without being further purified.

The (−)-(9bR*,13aR*)-2,7-dioxo-1,4,5,7,8,10,11,12,13,13a-decahydro-2H-pyrrolo[2',1':3,4]pyrazino[2,1-i]indole is produced in an analogous manner, starting from 2.3 g (10 mmol) of (−)-(9bR*,13aR*)-2-oxo-1,4,5,10,11,12,13,13a-octahydro-2H-pyrrolo[2',1':3,4]pyrazino[2,1-i]indole, and is obtained in the form of a foam, which can be further reacted without being further purified.

The starting materials can be manufactured, for example, as follows:

11.0 g of (±)-(9bR*,13aR*)-2-oxo-1,4,5,10,11,12,13,13a-octahydro-2H-pyrrolo[2',1':3,4-]pyrazino[2,1-i]indole are chromatographed in 22 portions each of 0.5 g on a Büchi glass column (600×50 mm) with tribenzoylcellulose as filler at about 7 bar with hexane/isopropanol (9:1) as eluant [detection: UV (230 nm)]. Concentration by evaporation of the top fractions yields the crude (+)-enantiomer in the form of an oil, which crystallises from diethyl ether/petroleum ether. Recrystallisation from diethyl ether/petroleum ether yields the pure (+)-(9bR*,13aR*)-2-oxo-1,4,5,10,11,12,13,13a-octahydro-2H-pyrrolo[2',1':3,4-]pyrazino[2,1-i]indole, which melts at 122°-123° $\{[\alpha]_D^{20} = +153.7° \pm 1.0°$ (CHCl$_3$; c=1)$\}$. After removal of the mixed fractions the (−)-enantiomer is finally eluted. Concentration of the final fractions by evaporation yields the crude (−)-enantiomer in the form of an oil, which crystallises from diethyl ether/petroleum ether. Recrystallisation from diethyl ether/petroleum ether yields the pure (−)-(9bR*,13aR*)-2-oxo-1,4,5,10,11,12,13,13a-octahydro-2H-pyrrolo[2',1':3,4-]pyrazino[2,1-i]indole, which melts at 122°-123° $\{[\alpha]_D^{20} = -154.8° \pm 1.0°$ (CHCl$_3$; c=1)$\}$.

EXAMPLE 4

2.21 g (9 mmol) of (+)-(9bR*,13aR*)-2,7dioxo-1,4,5,7,8,10,11,12,13,13a-decahydro-2H-pyrrolo[2',1':3,4]pyrazino[2,1-i]indole, dissolved in 100 ml of tetrahydrofuran, are hydrogenated with hydrogen in the presence of 220 mg of PtO$_2$ at room temperature under normal pressure until the absorption of hydrogen ceases. The catalyst is filtered off and the filtrate is concentrated in vacuo. The oily residue is dissolve in dichloromethane and the solution is then washed in succession with 0.1N hydrochloric acid and sodium hydrogen carbonate solution (5%). The organic phase is dried over sodium sulfate and concentrated by evaporation in vacuo. In this manner a crude product is obtained which chromatographed on 60 g of silica gel (0.040-0.063 mm) using dichloromethane and dichloromethane/methanol (99:1) as eluants. The desired product is obtained in crude form (oil) from the appropriate fractions. The oil is dissolved in 50 ml of water and the solution is extracted twice with 50 ml of diethyl ether in each case. The aqueous phase is treated with decolorising carbon at room temperature and then concentrated by evaporation in vacuo. The residue is dried for 36 hours under a high vacuum. The pure (+)-(9aR*,9bR*,13aR*)-2,7-dioxo-1,4,5,7,8,9,9a,10,11,12,13,13a-dodecahydro-2H-pyrrolo[2',1':3,4]pyrazino[2,1-i]indole is thus obtained in the form of a colourless oil, which contains 0.64 equivalents of water $\{[\alpha]_D^{20} = +53.7° \pm 1.0°$ (CHCl$_3$; c=1)$\}$.

The (−)-(9aR*,9bR*,13aR*)-2,7-dioxo-1,4,5,7,8,9,9a,10,11,12,13,13a-dodecahydro-2H-pyrrolo[2',1':3,4]pyrazino[2,1-i]indole is produced in an analogous manner, starting from 1.97 g (8 mmol) of (−)-(9bR*,13aR*)-2,7-dioxo-1,4,5,7,8,10,11,12,13,13-a-decahydro-2H-pyrrolo[2',1':3,4]pyrazino[2,1-i]indole, and is obtained in the form of a colourless oil, which contains 0.61 equivalents of water $\{[\alpha]_D^{20} = -52.1° \pm 1.0°$ (CHCl$_3$; c=1)$\}$.

EXAMPLE 5

Tablets, each containing 25 mg of the active ingredient, for example (9aR*,9bR*,13aR*)-2,7-dioxo-1,4,5,7,8,9,9a,10,11,12,13,13a-dodecahydro-2H-pyrrolo[2',1':3,4]pyrazino[2,1-i]indole, can be prepared as follows:

| Constituents (for 1000 tablets): | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Preparation

All of the solid ingredients are first of all forced through a sieve of 0.6 mm mesh size. The active ingredient, the lactose, the talc, the magnesium stearate and half of the starch are then mixed. The other half of the starch is suspended in 40 ml of water and this suspension is added to a boiling solution of the polyethylene glycol in 100 ml of water. The resulting starch paste is added to the main mixture which is then granulated, if necessary with the addition of water. The granulate is dried overnight at 35°, forced through a sieve of 1.2 mm mesh size and compressed to form tablets of approximately 6 mm diameter that are concave on both sides.

EXAMPLE 6

Tablets, each containing 50 mg of the active ingredient, for example (9aR*,9bR*,13aR*)-2,7-dioxo-1,4,5,7,8,9,9a,10,11,12,13,13a-dodecahydro-2H-pyrrolo[2',1':3,4]pyrazino[2,1-i]indole, are prepared as follows:

| Composition (for 10,000 tablets): | |
|---|---|
| active ingredient | 500.00 g |
| lactose | 140.80 g |
| potato starch | 274.70 g |
| stearic acid | 10.00 g |
| talc | 50.00 g |
| magnesium stearate | 2.50 g |
| colloidal silica | 32.00 g |
| ethanol | q.s. |

A mixture of the active ingredient, the lactose and 194.70 g of potato starch is moistened with an ethanolic solution of the stearic acid and granulated through a sieve. After the mixture has been dried, the remainder of the potato starch, the talc, the magnesium stearate and the colloidal silica are admixed and the mixture is compressed to form tablets each weighing 0.1 g which, if desired, may be provided with dividing notches for finer adjustment of the dose.

100 mg of active ingredient can be employed in an analogous manner.

EXAMPLE 7

Capsules, each containing 0.025 g of the active ingredient, for example (9aR*,9bR*,13aR*)-2,7-dioxo-1,4,5,7,8,9,9a,10,11,12,13,13a-dodecahydro-2H-pyrrolo[2′,1′:3,4]pyrazino[2,1-i]indole, can be prepared as follows:

| Composition (for 1000 capsules): | |
|---|---|
| active ingredient | 25.00 g |
| lactose | 249.00 g |
| gelatin | 2.00 g |
| cornstarch | 10.00 g |
| talc | 15.0 g |
| water | q.s. |

The active ingredient is mixed with the lactose, the mixture is uniformly moistened with an aqueous solution of the gelatin and granulated through a sieve having a mesh size of 1.2 to 1.5 mm. The granulate is mixed with the dried cornstarch and the talc and 300 mg portions are introduced into hard gelatin capsules (size 1).

EXAMPLE 8

In an analogous manner to that described in Examples 5 to 7 it is also possible to prepare pharmaceutical preparations that contain a different compound I or a pharmaceutically acceptable salt of a compound I, for example according to Examples 1 to 4, as active ingredient.

What is claimed is:

1. A compound of the formula I

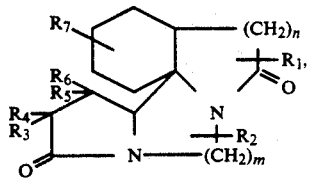

(I)

in which $R_1$, $R_2$, $R_3$, $R_5$ and $R_7$ are each, independent of the others, hydrogen or lower alkyl, m is 2, n is 1, and either $R_4$ and $R_6$ are each hydrogen or $R_4$ and $R_6$ together form an additional bond, in the free form or in the form of a salt.

2. A pharmaceutical preparation comprising a memory improving effective amount of a compound according to claim 1 in the free form or in the form of a pharmaceutically acceptable salt thereof in addition to a pharmaceutically acceptable adjunct.

3. A method of treating a memory disorder in a subject in need of such treatment, which method comprises administering to such subject a memory improving effective amount of a compound according to claim 1 in the free form or in the form of a pharmaceutically acceptable salt thereof.

4. A compound according to claim 1 of the formula I, in which $R_1$, $R_2$, $R_3$, $R_5$ and $R_7$ are each, independently of the others, hydrogen or lower alkyl, m is 2, n is 1, and $R_4$ and $R_6$ are each hydrogen, in free form or in form of a salt.

5. A compound according to claim 1 of the formula I, in which $R_1$, $R_2$, $R_3$, $R_5$ and $R_7$ are each hydrogen, m is 2, n is 1, and either $R_4$ and $R_6$ are each hydrogen or $R_4$ and $R_6$ together form an additional bond, in free form or in form of a salt.

6. A compound according to claim 1 of the formula I, in which $R_1$, $R_2$, $R_3$, $R_5$ and $R_7$ are each hydrogen, m is 2, n is 1, and $R_4$ and $R_6$ are each hydrogen, in free form or in form of a salt.

7. A compound as claimed in claim 1 being (9aR*,9bR*,13aR*)-2,7-Dioxo-1,4,5,7,8,9,9a,10,11,12,13,13a-dodecahydro-2H-pyrrolo[2′,1′:3,4]pyrazino[2,1-i]indole.

8. A compound as claimed in claim 1 being (9aR*,9bR*,13bR*)-2,7-Dioxo-1,4,5,7,10,11,12,13,13a-decahydro-2H-pyrrolo[2′,1′:3,4]pyrazino[2,1-i]indole.

9. A compound as claimed in claim 1 being the (+)enantiomer of (9aR*,9bR*,13aR*)-2,7-Dioxo-1,4,5,7,8,9,9a,10,11,12,13,13a-dodecahydro-2-pyrrolo[2′,1′:3,4]pyrazino[2,1-i]indole.

10. A compound as claimed in claim 1 being the (−)enantiomer of (9aR*,9bR*,13aR*)-2,7-Dioxo-1,4,5,7,8,9,9a,10,11,12,13,13a-dodecahydro-2-pyrrolo[2′,1′:3,4]pyrazino[2,1-i]indole.

11. A compound as claimed in claim 1 being (9aR*,9bS*,13aS*)-2,7-Dioxo-1,4,5,7,8,9,9a,10,11,12,13,13a-dodecahydro-2H-pyrrolo[[2′,1′:3,4]pyrazino[2,1-i]indole.

* * * * *

UNITED STATES PATENT AND TRADEMARK OFFICE
CERTIFICATE OF CORRECTION

PATENT NO. : 5,135,930

DATED : August, 4, 1992

INVENTOR(S) : WOLFGANG FROSTL, CESARE MONDADORI, DIETRICH STRUB ARMIN ZUST

It is certified that error appears in the above-identified patent and that said Letters Patent is hereby corrected as shown below:

Claim 8, Column 14, line 34 change "(9aR*, 9bR*, 13bR*)" to -- (9aR*,9bR*,13aR*)--

Signed and Sealed this

Seventeenth Day of August, 1993

Attest:

BRUCE LEHMAN

Attesting Officer

Commissioner of Patents and Trademarks